United States Patent
Van Dyke et al.

(10) Patent No.: US 9,895,178 B2
(45) Date of Patent: Feb. 20, 2018

(54) VARIABLE ANGLE LOCKING INSERT FOR INTRAMEDULLARY NAIL

(71) Applicant: Biomet Manufacturing, LLC, Warsaw, IN (US)

(72) Inventors: William Scott Van Dyke, Warsaw, IN (US); Paul Thomas Slagle, Leesburg, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 15/137,181

(22) Filed: Apr. 25, 2016

(65) Prior Publication Data

US 2016/0310177 A1 Oct. 27, 2016

Related U.S. Application Data

(60) Provisional application No. 62/152,338, filed on Apr. 24, 2015.

(51) Int. Cl.
*A61B 17/72* (2006.01)
*A61B 17/00* (2006.01)

(52) U.S. Cl.
CPC ............. *A61B 17/7241* (2013.01); *A61B 2017/00004* (2013.01)

(58) Field of Classification Search
CPC .......... A61B 17/7241; A61B 2017/00004
USPC ........................................................ 606/64
See application file for complete search history.

(56) References Cited

U.S. PATENT DOCUMENTS

| | | | |
|---|---|---|---|
| 6,783,529 B2 | 8/2004 | Hover et al. | |
| 8,066,706 B2 | 11/2011 | Schlienger et al. | |
| 8,157,802 B2 * | 4/2012 | Elghazaly | A61B 17/7241 606/64 |
| 8,303,590 B2 * | 11/2012 | Elghazaly | A61B 17/7241 606/64 |
| 8,465,489 B2 | 6/2013 | Schlienger et al. | |
| 8,790,343 B2 * | 7/2014 | McClellan | A61B 17/7241 606/64 |
| 2007/0233100 A1 | 10/2007 | Metzinger | |

OTHER PUBLICATIONS

Katthagen, J. C., et al., "Is there any advantage in placing an additional calcar screw in locked nailing of proximal humeral fractures ?", Orthop Traumatol Surg Res 101, Abstract, (Jun. 2015), 2 pgs.

* cited by examiner

*Primary Examiner* — Pedro Philogene
*Assistant Examiner* — David C Comstock
(74) *Attorney, Agent, or Firm* — Schwegman Lundberg & Woessner, P.A.

(57) ABSTRACT

A system including an intramedullary nail and an insert dimensioned to be positioned within the intramedullary nail. The insert can include a rotating component configured to rotate about a rotational axis transverse to a longitudinal axis of the intramedullary nail. The insert can be configured to receive a bone screw, rotate about the rotational axis as the bone screw is positioned at a selected angle of a plurality of angles relative to the intramedullary nail, and lock the bone screw at the selected angle.

20 Claims, 7 Drawing Sheets

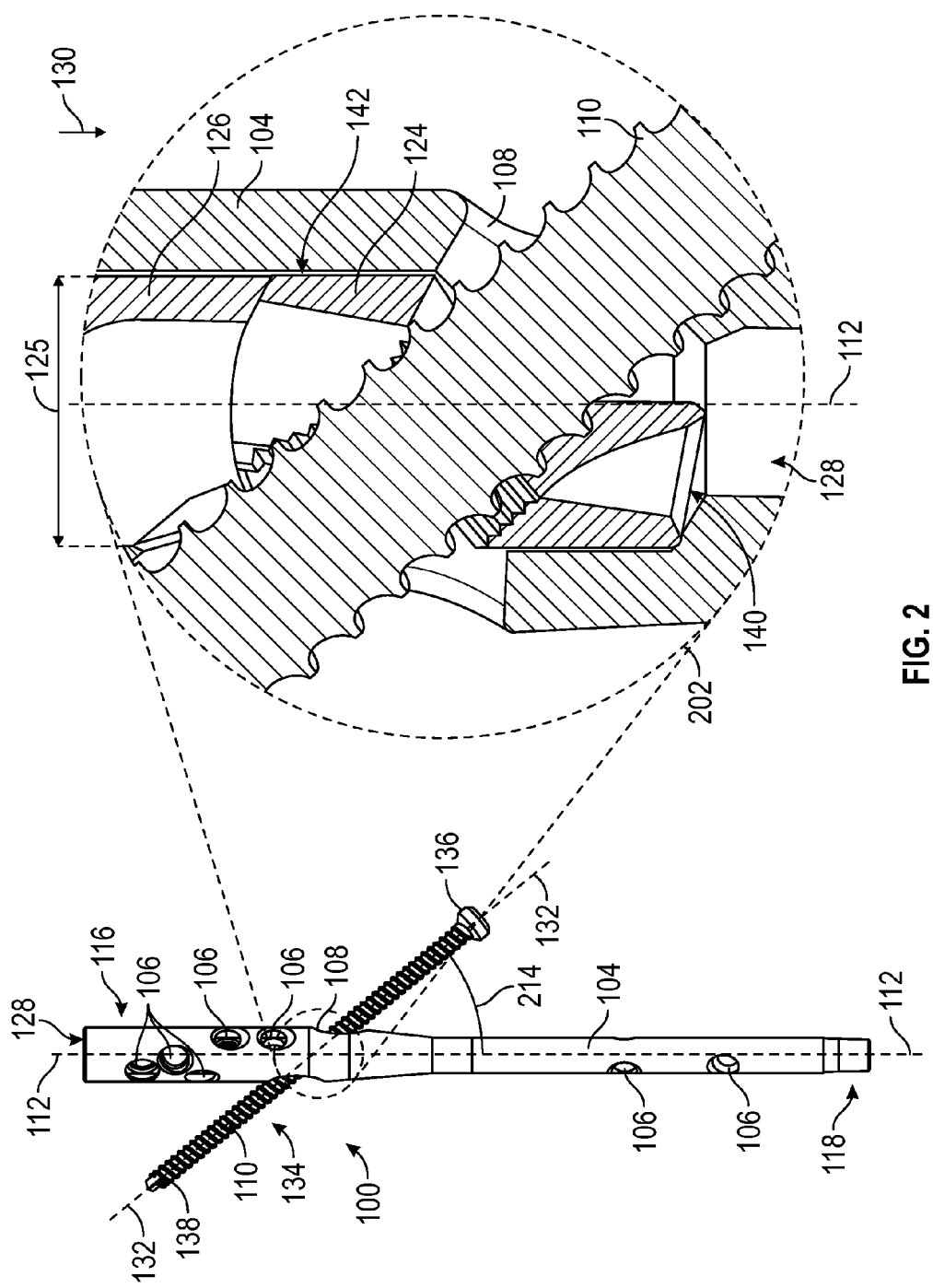

VARIABLE ANGLE LOCKING INSERT FOR INTRAMEDULLARY NAIL

CROSS-REFERENCE TO RELATED APPLICATIONS

This application claims the benefit of U.S. Provisional Application No. 62/152,338, filed on Apr. 24, 2015; the entire disclosure of which is incorporated herein by reference.

BACKGROUND

Intramedullary nailing has become a common treatment for fractures of long bones, including the femur, tibia, humerus, fibula, and for arthrodesis procedures for the ankle and knee joints. Anatomies can vary significantly in size and form from patient to patient. Many conventional intramedullary nail systems have fixed trajectories for bone screws. Some conventional systems require multiple set screws to lock the bone screw at a selected orientation. Some conventional systems only allow the bone screw closest to an end of the intramedullary nail to be locked. Some conventional systems require polymer sleeves surrounding the bone screw to provide a friction fit. Some conventional systems can result in bone screws that don't target beneficial portions of a specific patient's anatomy or that are not locked within the intramedullary nail. Due to the configuration of some conventional systems, the bone screw does not provide any additional biomechanical advantage.

OVERVIEW

To better illustrate the instrument disclosed herein, a non-limiting list of examples is provided here:

In Example 1, a system can be provided that includes an intramedullary nail, and an insert dimensioned to be positioned within the intramedullary nail, the insert including a rotating component configured to rotate about a rotational axis transverse to a longitudinal axis of the intramedullary nail, the insert configured to receive a bone screw, rotate about the rotational axis as the bone screw is positioned at a selected angle of a plurality of angles relative to the intramedullary nail, and lock the bone screw at the selected angle.

In Example 2, the system of Example 1 is optionally configured such that the intramedullary nail includes an elongated hole configured to receive the bone screw at any of the plurality of angles.

In Example 3, the system of Example 1 or Example 2 is optionally configured such that the insert is configured to be inserted into the intramedullary nail.

In Example 4, the system of any of Examples 1-3 is optionally configured such that the insert further includes a locking component configured to deliver a force to the rotating component such that the rotating component compresses around the bone screw to lock the bone screw at the selected angle.

In Example 5, the system of any of Examples 1-4 is optionally configured such that the plurality of angles has a range of at least 20 degrees.

In Example 6, the system of any of Examples 1-5 is optionally configured such that the rotating component includes at least one slot such that the rotating component is compressible into the at least one slot.

In Example 7, the system of Example 6 is optionally configured such that at least a portion of the at least one slot extends transverse to the longitudinal axis of the intramedullary nail.

In Example 8, a system can be provided that includes an intramedullary nail, and an insert configured to be positioned within the intramedullary nail, the insert including a rotating component configured to pivot about a rotational axis transverse to a longitudinal axis of the intramedullary nail, an insert through bore configured to align with a nail through bore of the intramedullary nail, and a locking mechanism positioned at a proximal end of the rotating component, the nail through bore and the insert through bore configured to receive a bone screw, the rotating component configured to rotate about the rotational axis as the bone screw is positioned at a selected angle, and the locking mechanism configured to lock the bone screw at the selected angle.

In Example 9, the system of Example 8 is optionally configured such that the rotating component includes a non-metal material.

In Example 10, the system of Example 8 is optionally configured such that the rotating component includes a resorbable material.

In Example 11, the system of Example 8 is optionally configured such that the rotating component includes titanium.

In Example 12, the system of any of Examples 8-10 is optionally configured such that the insert through bore is configured to align with the nail through bore to define a channel to allow passage of the bone screw therethrough.

In Example 13, the system of any of Example 8-12 is optionally configured such that the insert through bore includes one or more internal threads configured to engage one or more external threads of the bone screw.

In Example 14, the system of any of Examples 8-13 is optionally configured such that the insert defines a variable angle screw trajectory with two rotational degrees of freedom.

In Example 15, the system of any of Examples 8-14 is optionally configured such that the rotating component is configured to rotate about the longitudinal axis of the intramedullary nail.

In Example 16, a system can be provided that includes an intramedullary nail including a nail longitudinal axis and including an inner diameter defining a nail lumen, and an insert dimensioned to be positioned within the nail lumen, the insert including a rotating component configured to rotate about a rotational axis transverse to the nail longitudinal axis to provide a variable angle trajectory for a bone screw, and a locking mechanism configured to compress the rotating component to lock the bone screw at a patient-specific angle.

In Example 17, the system of Example 16 is optionally configured such that the intramedullary nail is a humeral nail and the bone screw is a calcar screw, such that the insert is configured to lock the calcar screw at the patient-specific angle corresponding to a patient-specific calcar area of a patient's humeral head.

In Example 18, the system of Example 16 or Example 17 is optionally configured such that the insert is configured to be positioned entirely within the nail lumen of the intramedullary nail.

In Example 19, the system of any of Examples 16-18 is optionally configured such that the insert forms a lumen along the nail longitudinal axis.

In Example 20, the system of any of Examples 16-19 is optionally configured such that the rotating component is configured to rotate about the nail longitudinal axis to provide the variable angle trajectory for the bone screw.

In Example 21, a system can be provided that includes an intramedullary nail including a nail through bore, the intramedullary nail including an inner diameter defining a longitudinally extending nail lumen, and a variable angle locking insert dimensioned to be positioned within the nail lumen, the insert including an insert through bore formed in the insert through a nail hole of the intramedullary nail, such that the insert can receive a bone screw at any of a plurality of angles and lock the bone screw at a selected angle of the plurality of angles.

In Example 22, the system of Example 21 is optionally configured such that the insert includes a non-metal material.

In Example 23, the system of Example 21 or Example 22 is optionally configured such that the insert includes a resorbable material.

In Example 24, the system of any of Examples 21-23 is optionally configured such that the nail hole includes an elongated through bore, an opening of the elongated through bore having a longitudinal axis substantially parallel to a longitudinal axis of the intramedullary nail.

In Example 25, the system of any of Examples 21-24 is optionally configured such that the insert is configured to be inserted within the intramedullary nail.

In Example 26, the system of any of Examples 21-25 is optionally configured such that the insert is formed within the intramedullary nail.

In Example 27, the system of any of Examples 21-26 is optionally configured such that the insert forms a lumen.

In Example 28, the system of any of Examples 21-26 is optionally configured such that the insert forms a lumen.

In Example 29, the system of any of Examples 21-28 is optionally configured such that the insert is configured to be positioned entirely within the intramedullary nail.

In Example 30, the system of any of Examples 21-29 is optionally configured such that the intramedullary nail is a humeral nail and the bone screw is a calcar screw, such that the insert is configured to lock the calcar screw at the selected angle corresponding to a patient-specific calcar area of a patient's humeral head.

In Example 31, the system of any of Examples 21-30 is optionally configured such that a distal portion of the insert includes a chamfer configured to engage a taper of the intramedullary nail.

In Example 32, the system of any of Examples 21-31 is optionally configured such that a proximal end of the insert includes a slant configured to engage a distal portion of a locking component.

In Example 33, the system of Example 32, further including the locking component configured to lock the insert within the intramedullary nail.

In Example 34, the apparatus, system, or method of any one or any combination of Examples 1-33 can optionally be configured such that all elements or options recited are available to use or select from.

These and other examples and features of the present devices, systems, and methods will be set forth in part in the following Detailed Description. This overview is intended to provide a summary of subject matter of the present patent application. It is not intended to provide an exclusive or exhaustive description of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

FIG. 2 is a perspective view of the variable angle locking system of FIG. 1 in a second position and a corresponding magnified cross-sectional view, in accordance with at least one example of the present disclosure.

DETAILED DESCRIPTION

Figure 1:
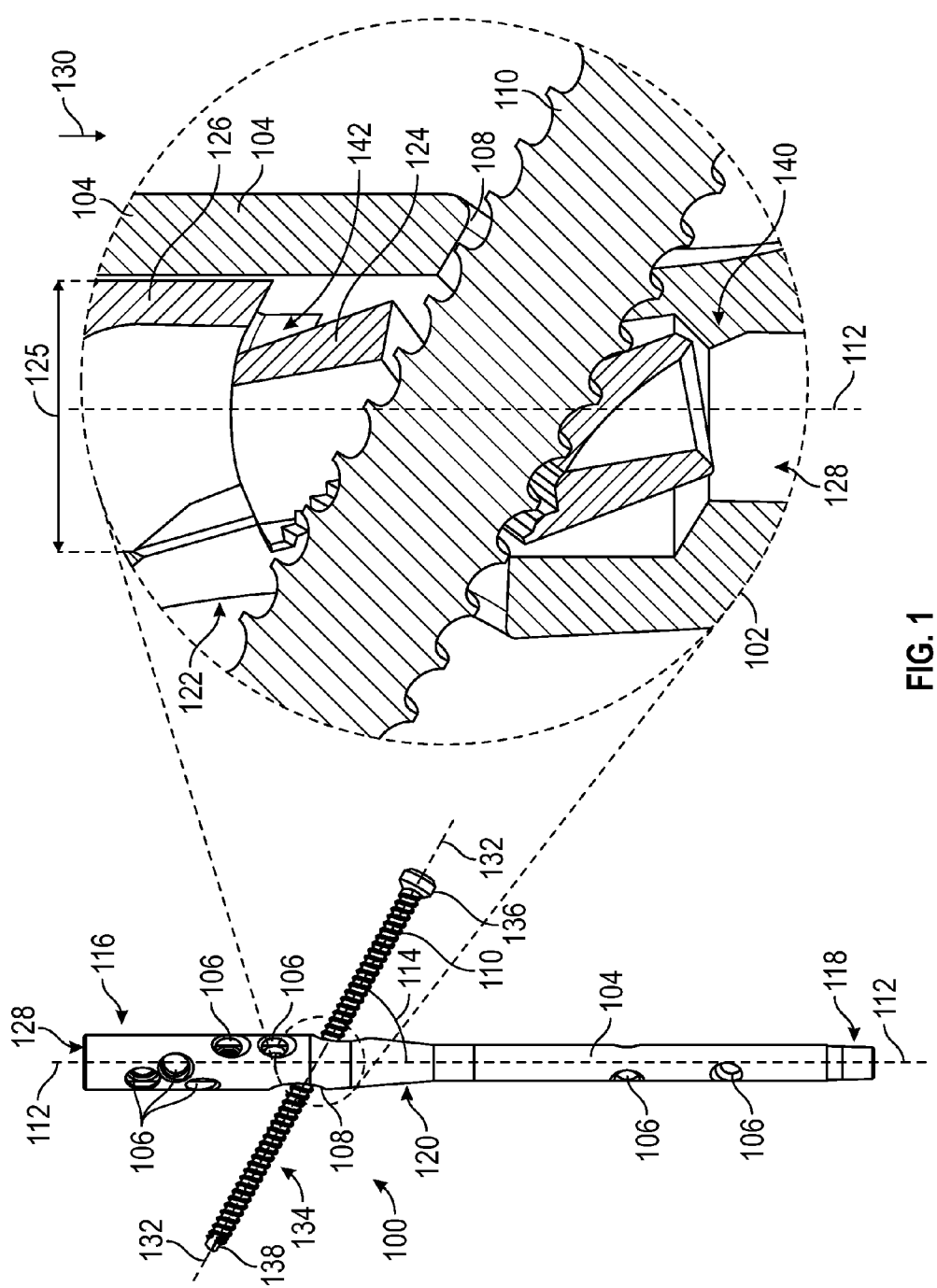
FIG. 1 is a perspective view of a variable angle locking system in a first position and a corresponding magnified cross-sectional view, in accordance with at least one example of the present disclosure.

A variable angle locking system can generally include an intramedullary nail and an insert configured to be positioned within the intramedullary nail. The insert can include a rotating component that can rotate about one or more axes to provide a variable angle trajectory, such that a bone screw can be positioned through a nail hole of the intramedullary nail at any one of a plurality of selectable angles. The insert can further include a locking component that can lock the rotating component in a selected orientation, so as to lock the bone screw at a selected orientation.

The variable angle locking system can provide a variable angle locking screw trajectory, such that the system can lock a bone screw at any of a plurality of angles. For example, the variable angle locking system can include a humeral nail and provide a variable angle trajectory for a calcar screw, so as to target a patient-specific calcar and lock the calcar screw in the desired orientation. For ease of understanding, the examples are primarily described with the humeral nail application in mind. As such, "proximal" and "distal" are relative and described with reference to the orientation of a humeral nail. However, it will easily be understood by one of ordinary skill in the art that some applications would require a reversal of this terminology due to a different orientation of an intramedullary nail. For example, while the insert may be positioned at the proximal end of a humeral intramedullary nail, in the case of an ankle arthrodesis procedure the insert may be placed at the distal end of the nail, in which case the "proximal" and "distal" orientation of the insert can be reversed as well.

In another example, the variable angle locking system can include a hip fracture nail and provide a variable angle trajectory for a lag screw, so as to target a patient-specific femoral head and lock the lag screw in the desired orientation. Since conventional hip fracture nail systems offer two different nails with different lag screw angles in the femoral head, the variable angle locking system can reduce the required inventory of hip fracture nails and enable the surgeon to avoid deciding which nail to use. In another example, the variable angle locking system can include a tibial nail and provide a variable angle trajectory for bone screws to better target quality of bone in the tibial plateau of a specific patient's anatomy and lock the bone screws in the desired orientation. In the example of an ankle arthrodesis procedure, the variable angle locking system can provide a variable angle trajectory for bone screws, so as to target quality bone stock in the calcaneus and the talus of a specific patient's anatomy, and to lock the bone screws in the desired orientation. In another example, the variable angle locking system can include a retrograde femoral nail and provide a variable angle trajectory for bone screws to target the center of each condyle.

Further areas of applicability will become apparent from the description provided herein. The description and specific examples in this summary are intended for purposes of illustration only and are not intended to limit the scope of the present disclosure.

FIG. 1 is a perspective view of a variable angle locking system 100 in a first position and a corresponding magnified cross-sectional view 102, in accordance with at least one example of the present disclosure. In the illustrated example, an intramedullary nail 104 can include a plurality of through bores or holes 106 and an elongated nail hole or through bore 108. The elongated nail hole 108 can be configured to receive a bone screw 110 at a plurality of angles relative to a nail longitudinal axis 112 of the intramedullary nail 104, including a first selected angle 114.

In some examples, the intramedullary nail 104 can extend along the nail longitudinal axis 112 from a proximal end 116 to a distal end 118. In at least one example, the intramedullary nail 104 can include a tapered portion 120 between the proximal end 116 and the distal end 118. In some examples, the intramedullary nail 104 can include more or less holes 106 than the illustrated example. In some examples, the intramedullary nail 104 can form a lumen (nail lumen 128) along the nail longitudinal axis 112 from the proximal end 116 to the distal end 118. In some examples, the nail lumen 128 is defined by an inner diameter of the intramedullary nail 104. In at least one example, the intramedullary nail 104 can form a lumen along the nail longitudinal axis 112 for only a portion of the length of the intramedullary nail 104. For example, the intramedullary nail 104 can form a lumen at the proximal end 116, but not at the distal end 118. Alternatively, the intramedullary nail 104 can form a lumen along its entire longitudinal length and can accommodate a bead-tipped guidewire.

As can be seen in the exploded view 102, in some examples an insert 122 can be dimensioned to fit within an inner diameter 125 of the intramedullary nail 104. For example, the insert 122 can be positioned within the lumen 128 of the intramedullary nail 104. In the illustrated example, the insert 122 is configured to be positioned entirely within the intramedullary nail 104.

In some examples, the insert 122 can include a rotating component 124 and a locking component 126. In some examples, the rotating component 124 can be configured to rotate about a rotational axis that is transverse to the nail longitudinal axis 112 of the intramedullary nail 104. In at least one example, the rotational axis is normal or perpendicular to the nail longitudinal axis 112. In some examples the locking component 126 can be configured to apply or transfer a force 130 to the rotating component 124 along the nail longitudinal axis 112 of the intramedullary nail 104. In at least one example, the locking component 126 can cause the rotating component 124 to compress about the bone screw 110 to lock the bone screw 110 at the first selected angle 114. In at least one example, the locking component 126 causes the rotating component 124 to rotate about a rotational axis that is transverse to the nail longitudinal axis 112. The bone screw 110 may be positioned in a specific orientation (e.g., the first selected angle 114) and then the locking component 126 may cause the rotating component 124 to clamp down on the bone screw 110 to secure the bone screw at the specific orientation. As the locking component 126 applies a force 130 to the rotating component 124 to cause the rotating component 124 to rotate and eventually clamp down on the bone screw 114, the rotating component may not cause the bone screw 110 to rotate away from the specific orientation (e.g., the first selected angle 114). In other words, the bone screw 110 can remain in the specific orientation as the rotating component 124 rotates and ultimately locks the bone screw 110 in place.

In some examples, the locking component 126 can comprise a lumen and the lumen can accommodate a bead-tipped guidewire. In at least one example, the locking component 126 can comprise a plurality of holes corresponding to at least a portion of the plurality of holes 106 at the proximal head 116 of the intramedullary nail 104. In at least one example, the locking component 126 can comprise Biomet CoreLock™ technology. In at least one example, the locking component 126 can comprise the lockable intramedullary nail technology described in U.S. Pat. No. 9,320,551, which is hereby incorporated by reference in its entirety. In at least one example, the locking component 126 remains in the intramedullary nail 104 after the rotating component 124 has compressed to lock the bone screw in place. In at least one example, the locking component 126 continues to apply a force to the rotating component 124 even after the rotating component 124 has compressed to lock the bone screw in place. In at least one example, the locking component 126 prevents the rotating component 124 from uncompressing or moving proximally after the rotating component 124 has compressed to lock the bone screw in place.

In some examples, the rotating component 124 can be locked in a selected orientation between the intramedullary nail 104 and the locking component 126. For example, the rotating component 124 can be secured by the intramedullary nail 104 at a distal end 140 of the rotating component 124 and by the locking component 126 at a proximal end 142 of the rotating component. In at least one example, the rotating component 124 can be configured to engage an inner diameter of the tapered portion 120 of the intramedullary nail 104. For example, in the illustrated example, the lumen 128 of the intramedullary nail 104 can have a smaller diameter at the tapered portion 120 than at the proximal end 116, and the rotating component 124 can be prevented from moving toward the distal end 118 of the intramedullary nail 104 due to the reduced inner diameter at the tapered portion 120. In at least one example, the intramedullary nail 104 can include an edge, shelf, or other inner diameter feature to prevent movement of the rotating component 124 toward the distal end 118 of the intramedullary nail 104.

In some examples, the range of angle trajectories can be restricted by the dimensions of the elongated nail hole 108. For example, the rotating component 124 can be configured to rotate from an orientation where the bone screw 110 meets a distal end of the elongated nail hole 108 to an orientation where the bone screw 110 meets a proximal end of the elongated nail hole 108. In some examples, the elongated nail hole 108 can form an oval or an ellipse. In at least one example, the elongated nail hole 108 can be elongated relative to the outer diameter of the bone screw 110 along at least two axes of the face of the elongated nail hole 108. In at least one example, the elongated nail hole 108 can form a shape other than a circle or an ellipse at its face.

In at least one example, the first selected angle 114 can be a patient-specific angle that can be chosen based on the patient's anatomy. In some examples, the first selected angle 114 can be the angle of a bone screw longitudinal axis 132 relative to the nail longitudinal axis 112. In at least one example, the bone screw longitudinal axis 132 can extend along a shaft 134 of the bone screw 110 from a head 136 to a tip 138 of the bone screw 110. In some examples, at least a portion of the shaft 134 of the bone screw 110 can be externally threaded.

FIG. 2 is a perspective view of the variable angle locking system 100 of FIG. 1 in a second position and a corresponding magnified cross-sectional view 202, in accordance with at least one example of the present disclosure. In the illustrated example, the rotating component 124 is shown in a second position, having rotated about the rotational axis relative to the example shown in FIG. 1, to create a second bone screw trajectory of the plurality of bone screw trajectories. In the illustrated example, the bone screw 110 is positioned at a second selected angle 214.

In the illustrated example, the first and second selected angles 114, 214 can represent the maximum and minimum bone screw trajectories provided by the insert 122. In some examples, the insert 122 can be configured to lock the bone screw 110 at any angle between the minimum angle and the maximum angle. In some examples, the maximum angle can be greater or less than the example first selected angle 114 shown in FIG. 1. In some examples the minimum angle can be greater or less than the example second selected angle 214 shown in FIG. 2. In some examples, the rotating component 124 can provide a variable angle bone screw trajectory range of 20 degrees. In at least one example, the rotating component 124 can provide a variable angle bone screw trajectory range of less than 20 degrees. In at least one example, the rotating component 124 can provide a variable angle bone screw trajectory range of at least 20 degrees. In at least one example, the rotating component 124 can provide a variable angle bone screw trajectory range of at least 30 degrees. In at least one example, the rotating component 124 can provide a variable angle bone screw trajectory of 40 degrees or more.

Figure 3B:
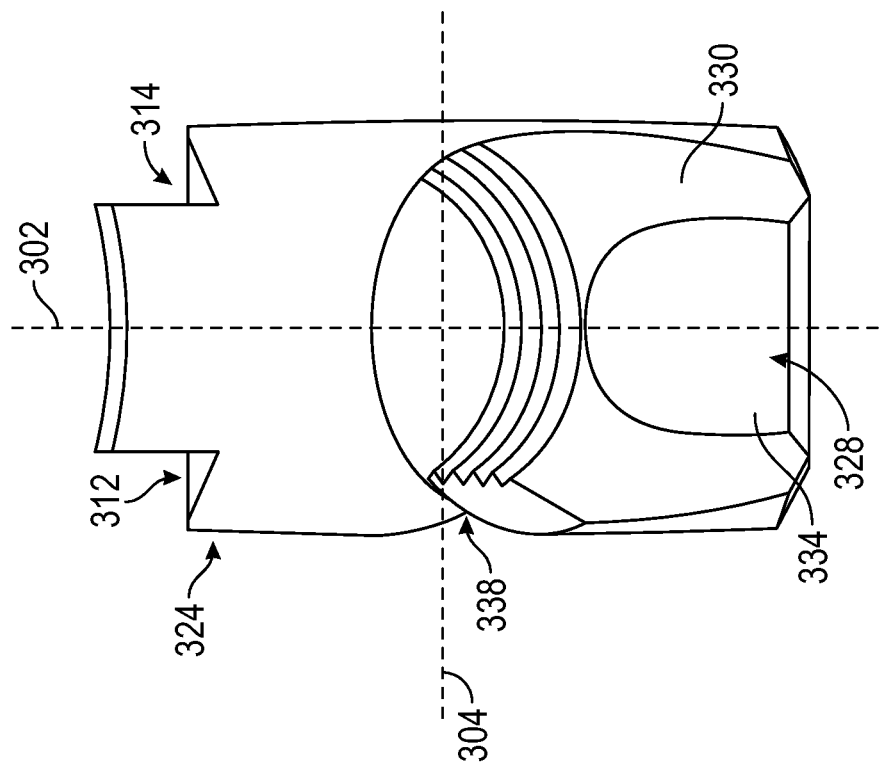
FIGS. 3A-3E are various views of a rotating component of a variable angle locking system in accordance with at least one example of the present disclosure.
Figure 3A:
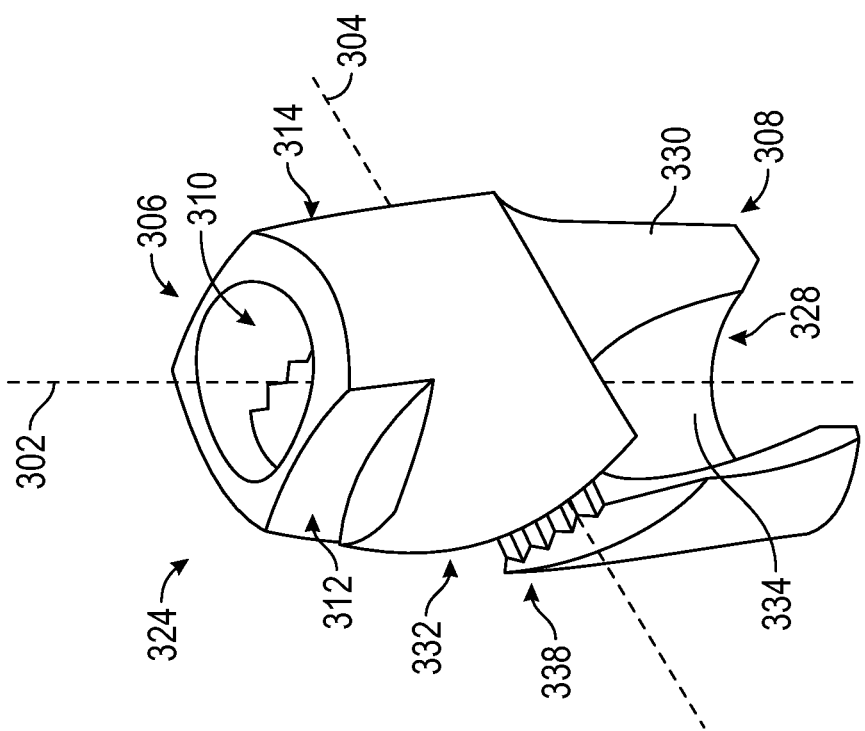
Figure 3E:
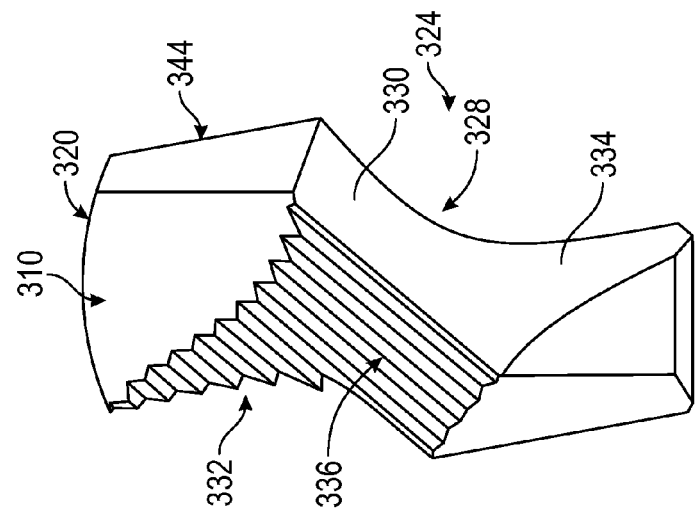
Figure 3D:
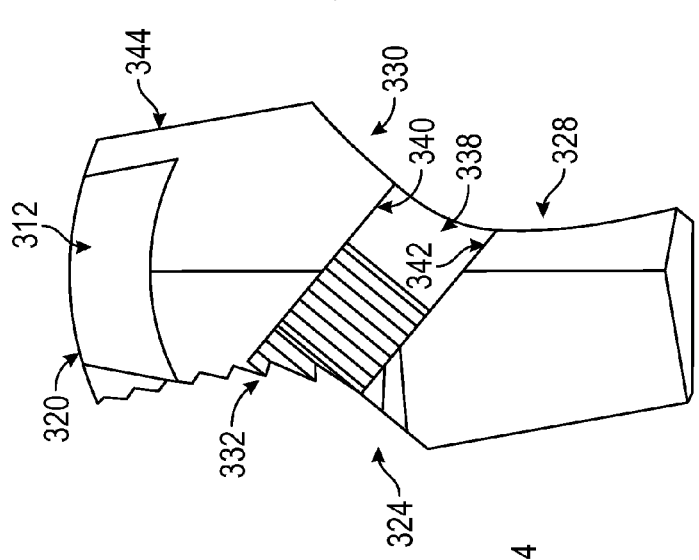
Figure 3C:
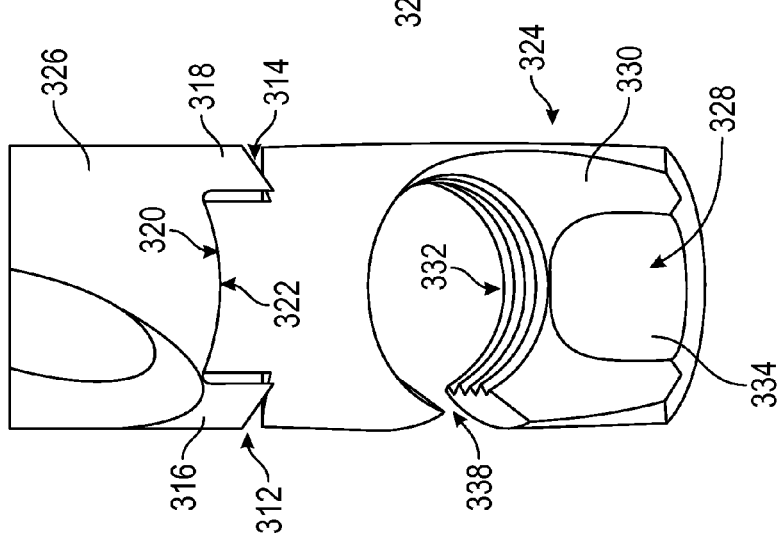

FIGS. 3A-3E are various views of a rotating component 224 of a variable angle locking system, such as the variable angle locking system 100, described with reference to FIGS. 1 and 2. Specifically, FIG. 3A is an isometric view, FIGS. 3B and 3C are front views, FIG. 3D is a side view, and FIG. 3E is a cross-sectional view of FIG. 3D. In at least one example, the rotating component 324 can include an insert longitudinal axis 302 that corresponds to the nail longitudinal axis 112. In some examples, the rotating component 324 can include a rotational axis 304 transverse to the insert longitudinal axis 302 or the nail longitudinal axis 112. In at least one example, the rotational axis 304 can be substantially perpendicular to the insert longitudinal axis 302 or the nail longitudinal axis 112. In some examples, the rotating component 324 can be configured to rotate about the rotational axis 304 while positioned within the intramedullary nail 104.

In some examples, the rotating component 324 can extend along the insert longitudinal axis 302 from a proximal end 306 to a distal end 308. In some examples the rotating component 324 can include an insert lumen 310. For example, the insert lumen 310 can allow the intramedullary nail 104 to accept a bead-tipped guidewire.

In some examples, the rotating component 324 can include one or more engaging members 312, 314 configured to engage a locking component 326 with one or more corresponding engaging members 316, 318. In at least one example, the one or more engaging members 312, 314 can comprise cutouts or edges. In at least one example, the one or more engaging members 312, 314 can comprise semicircular edges or cutouts. In some examples, the one or more corresponding engaging members 316, 318 of the locking component 326 can restrict rotational movement of the rotating component 324 about the insert longitudinal axis 302 or the nail longitudinal axis 112. In at least one example, the one or more corresponding engaging members 316, 318 can prevent rotational movement of the rotating component 324 about the insert longitudinal axis 302 or the nail longitudinal axis 112.

In some examples, a proximal surface 320 of the rotating component 324 can be configured to engage a distal surface 322 of the locking component 326. In some examples, the locking component 326 can be configured to transfer the force 130 to the rotating component 324 through contact of surfaces 320 and 322. In at least one example, the locking component 326 can be configured to transfer the force 130 to the rotating component 324 through contact of corresponding engaging portions 316, 318 with engaging portions 312, 314. In at least one example, the proximal surface 320 can be convex about the rotational axis 304 to correspond to the distal surface 322 of the locking component 326. For example, the convex proximal surface 320 can allow the rotating component 324 to rotate about the rotational axis 304, such that the convex proximal surface 320 moves along the concave distal surface 322 of the locking component 326.

In some examples, the rotating component 324 can include an insert hole or through bore 328 configured to receive the bone screw 110. In some examples, the insert hole 328 is configured to align with the nail hole 108 to define a channel to allow passage of the bone screw 110 therethrough. In some examples, the insert hole 328 can include an entrance portion 330 and an exit portion 332. In at least one example, the entrance portion 330 can include a lumen 334 configured to receive the bone screw 110. In at least one example, the lumen 334 can be sized to allow the bone screw 110 to enter in at a valgus angle when the rotating component is positioned at a varus angle. In some examples, the insert hole 328 can include a smooth surface near the entrance portion 330. In some examples, the insert hole 328 can include one or more threads or interdigitated serrations 336 configured to engage the bone screw 110. In at least one example, the interdigitated serrations 336 can engage the threads of the bone screw 110 when the rotating component 324 is compressed, locking the bone screw 110 at the selected angle 114, 214. In at least one example, the insert hole 328 can include internal threads configured to engage the bone screw 110.

In some examples, the rotating component 324 can include at least one slot 338. In some examples, at least a portion of the slot 338 can extend transverse to the insert longitudinal axis 302 or the nail longitudinal axis 112. In at least one example, the slot 338 can include a proximal wall 340 and a distal wall 342. In some examples, the rotating component 324 can be configured to compress into the slot 338 in response to the force 130 provided by the locking component 326. In at least one example, the rotating component 324 can be configured to compress such that the proximal wall 340 moves distally. In at least one example, the rotating component 324 can be configured to compress such that the proximal wall 340 and the distal wall 342 move closer together, and the width of the slot 338 is reduced. In at least one example, the rotating component 324 can be configured to compress such that the proximal wall 340 and the distal wall 342 touch.

In some examples, the rotating component 324 is not cylindrical. In some examples, the rotating component 324 can taper at the proximal end 306 to facilitate rotation about the rotational axis 304. In some examples, the rotating component 324 can taper at the proximal end 306 in one direction, such that the taper is visible from a side view (e.g., FIGS. 3D and 3E) but not from a front view (e.g., FIGS. 3B and 3C). In at least one example, the rotating component 324 can include a taper wall 344 at the proximal end 306 to facilitate rotation of the rotating component 324 about the rotational axis 304.

In some examples, the rotating component 324 can comprise titanium. In some examples, the rotating component 324 can comprise metal, non-metal, resorbable material, a composite material, or the like. In at least one example, the rotating component 324 can be formed in the intramedullary nail 104. In some examples, the rotating component 324 can be formed separately and subsequently inserted into the intramedullary nail 104.

In some examples, the bone screw 110 can be inserted into the elongated hole 108 of the intramedullary nail, and the entrance portion 330 of the insert hole 328 at any of a plurality of angles such that the bone screw 110 extends out the exit portion 332 of the insert hole 328. The bone screw 110 and the rotating component 324 can be rotated about the rotational axis 324 to achieve a selected angle of the bone screw 110, for example, a patient-specific angle or bone screw trajectory. The locking component 326 can then be used to provide the force 130 to the rotating component 324 to compress the rotating component 324 into the slot 338, such that at least a portion of the plurality of interdigitated serrations 336 engage the threads of the bone screw 110 to lock the bone screw 110 at the selected angle.

Figure 4C:
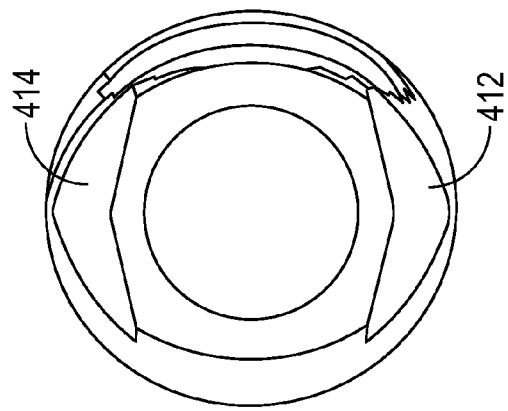
FIGS. 4A-4C are various views of a rotating component of a variable angle locking system in accordance with at least one example of the present disclosure.
Figure 4B:
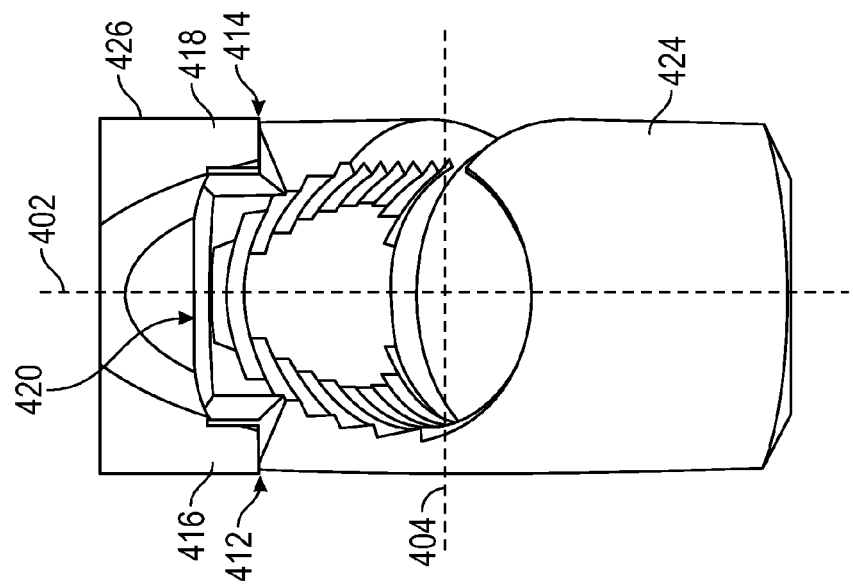
Figure 4A:
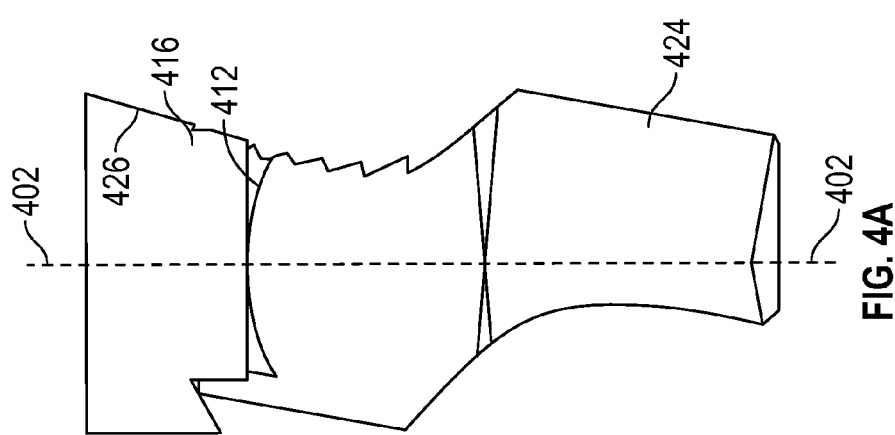

FIGS. 4A-4C are various views of a rotating component 424 of a variable angle locking system (such as the variable angle locking system 100 of FIGS. 1 and 2). Specifically, FIG. 4A is a side view, FIG. 4B is a back view, and FIG. 4C is a top view. In some examples, the rotating component 424 can rotate about an insert longitudinal axis 402 (or the nail longitudinal axis 112) and a rotational axis transverse to the insert longitudinal axis 402 (or the nail longitudinal axis 112). That is, the rotating component 424 can define a variable angle screw trajectory having variation in two degrees of freedom, allowing a cone of angulation for the screw 110 possible in two dimensions.

In some examples, a proximal surface 420 of the rotating component 424 can be spherical. In some examples, a distal surface 422 of a locking component 426 can be substantially flat. In some examples, the rotating component 424 can include one or more engaging members 412, 414 configured to engage one or more corresponding engaging members 416, 418 of the locking component 426. In at least one example, the one or more engaging members 412, 414 can comprise cutouts or edges. In at least one example, the one or more engaging member 412, 414 can comprises angled edges or cutouts corresponding to the angle of rotation allowable about the insert longitudinal axis 402 (or the nail longitudinal axis 112). In some examples, the one or more corresponding engaging members 416, 418 of the locking component 426 can restrict rotational movement of the rotating component 424 about the insert longitudinal axis 402 or the nail longitudinal axis 112. In at least one example, the one or more corresponding engaging members 416, 418 can prevent rotational movement of the rotating component 424 about the insert longitudinal axis 402 (or the nail longitudinal axis 112) beyond a maximum rotation. In at least one example, the corresponding engaging members 416, 418 can prevent rotational movement of the rotating component 424 about the insert longitudinal axis 402 (or the nail longitudinal axis 112) beyond 5 degrees in either direction. In at least one example, one or more surfaces of the rotating component 424 can be roughened to increase friction between the rotating component 424 and other components. In at least one example, surfaces 412, 414 can be roughened to provide a more secure mechanical lock.

Figure 5B:
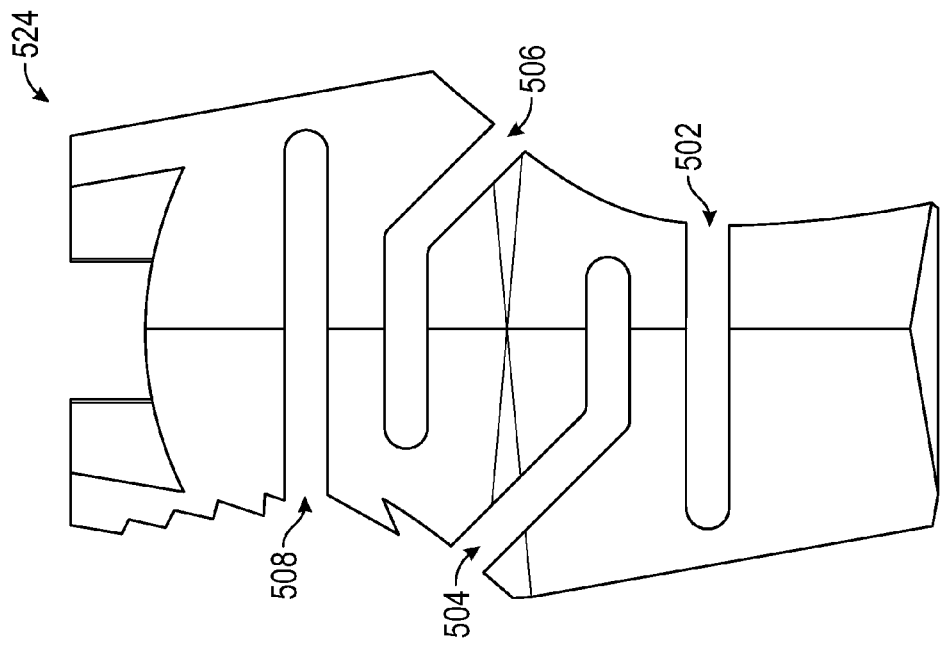
FIGS. 5A and 5B are two views of a rotating component of a variable angle locking system in accordance with at least one example of the present disclosure.
Figure 5A:
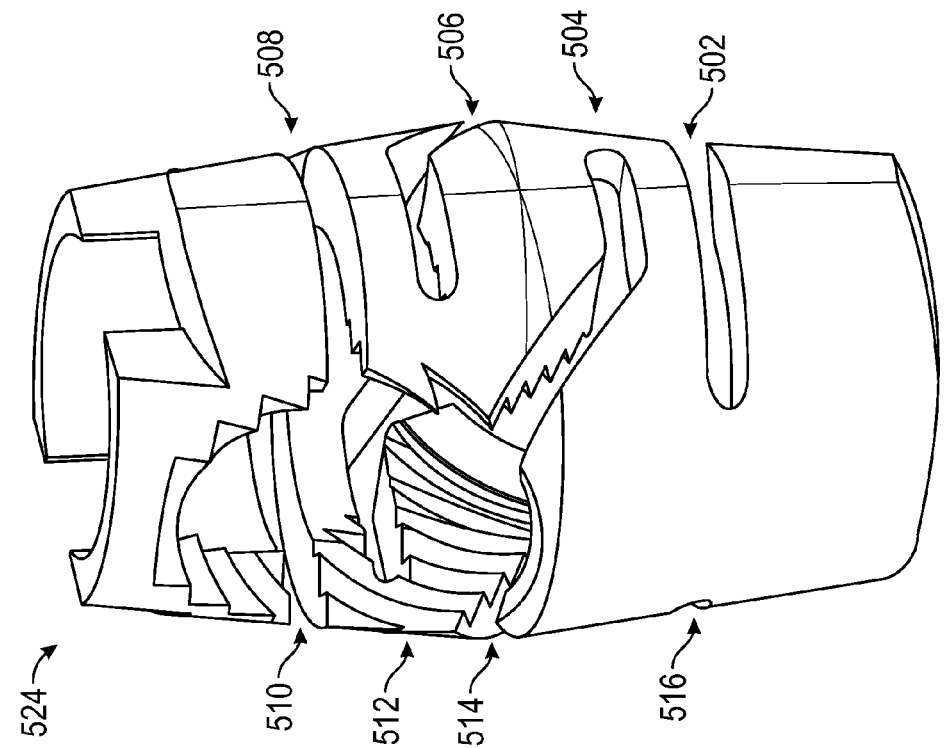

FIGS. 5A and 5B are two views of a rotating component 524 of a variable angle locking system (such as the variable angle locking system 100 of FIGS. 1 and 2). Specifically, FIG. 5A is an isometric view of the rotating component 524, and FIG. 5B is a side view of the rotating component 524. In the illustrated example, the rotating component 524 can share many features of rotating components of FIGS. 1-4. In some examples, the rotating component 524 can include a plurality of slots 502, 504, 506, 508, 510, 512, 514, 516. In some examples, the rotating component 524 can include more or less slots 502-516 than the illustrated example. In some examples, the rotating component 524 can include slots 502-516 on both sides of the rotating component 524. In at least one example, the plurality of slots 502-516 can be symmetrically distributed on the rotating component 524.

In some examples, some of the plurality of slots 502-516 can extend transverse to the nail longitudinal axis 112. In some examples, a first group 504, 506, 512, 514 of the plurality of slots 502-516 can be non-parallel to a second group 502, 508, 510, 516 of the plurality of slots 502-516. In some examples, all of the plurality of slots 502-516 can be parallel. In some examples, one or more of the plurality of slots 502-516 can extend in more than one direction. In some examples, the rotating component 524 can include a plurality of slots 502-516 to facilitate even compression of the rotating component 524 about the bone screw 110.

Figure 6:
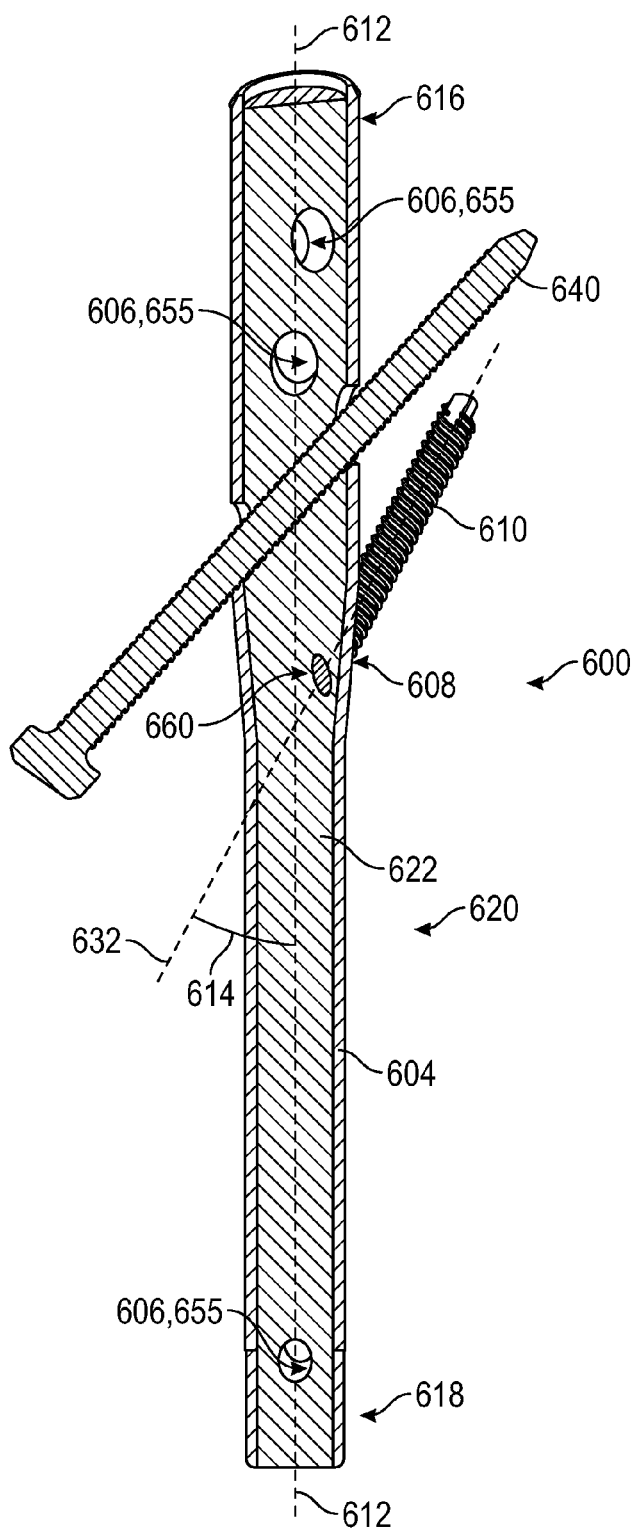
FIG. 6 is a cross-sectional view of a variable angle locking system, in accordance with at least one example of the present disclosure.

FIG. 6 is a cross-sectional view of a variable angle locking system 600, in accordance with at least one example of the present disclosure. In the illustrated example, an intramedullary nail 604 can include a plurality of through bores or holes 606 and an elongated nail hole or through bore 608. The elongated nail hole 608 can be configured to receive a bone screw 610 at a plurality of angles relative to a nail longitudinal axis 612 of the intramedullary nail 604, including a selected angle 614.

In some examples, the intramedullary nail 604 can extend along the nail longitudinal axis 612 from a proximal end 616 to a distal end 618. In at least one example, the intramedullary nail 604 can include a tapered portion 620 between the proximal end 616 and the distal end 618. In some examples, the intramedullary nail 604 can include more or less holes 606 than the illustrated example. In some examples, the intramedullary nail 604 can form a lumen (for an example, see lumen 128 of FIGS. 1 and 2) along the nail longitudinal axis 612 from the proximal end 616 to the distal end 618. In at least one example, the intramedullary nail 604 can form a lumen along the nail longitudinal axis 612 for only a portion of the length of the intramedullary nail 604. For example, the intramedullary nail 604 can form a lumen at the proximal end 616, but not at the distal end 618.

In the illustrated example, an insert 622 can be dimensioned to fit within the intramedullary nail 604. In some examples, the insert 622 can be configured to be positioned entirely within the intramedullary nail 604. In some examples, the insert 622 can be configured to be inserted into the intramedullary nail 604. In some examples, the insert 622 can be configured to be formed within the intramedullary nail 604. In at least one example, an inner diameter of the intramedullary nail 604 defines a nail lumen, and the insert 622 is positioned within the nail lumen.

In some examples, the insert 622 can provide a variable angle screw trajectory for the bone screw 610. In some examples, the insert 622 can be configured to have one or more holes 655, 660 drilled into the insert 622 through one or more holes 606, 608 of the intramedullary nail 604. In some examples, the insert can be configured to receive a plurality of bone screws 610, 640. In some examples, the insert can be configured to have an insert through bore or hole 660 drilled into the insert 622 through the elongated nail hole 608 at the selected angle 614, and the bone screw 610 could be inserted into the predrilled insert hole 660. In such an example, the insert 622 can provide a variable angle bone screw trajectory and lock the bone screw 610 at the selected angle 614 without additional locking components. For example, the insert 622 can lock the bone screw 610 at the selected angle 614 of the plurality of angles without the use of a set screw. In at least one example, the bone screw 610 can be drilled into the insert 622, without a predrilled insert hole 660. In some examples, the range of the variable angle trajectory can be restricted by the dimensions of the elongated hole 608. In some examples, the elongated hole 608 can be dimensioned to allow for a cone of angulation for the bone screw 610 possible in two dimensions. For example, the elongated hole 608 can be elongated relative to the bone screw 610 in more than one direction, such that the elongated hole 608 allows for variation of the bone screw trajectory in two degrees of freedom.

In some examples, the insert 622 can comprise a nonmetal material. In some examples, the insert 622 can comprise a resorbable material. In some examples, the insert 622 could retain 80% of its mechanical strength over the first eight weeks it is implanted. In some examples, the insert 622 can have a distal end that is chamfered to match a distal end of the intramedullary nail 604. In some examples, the insert 622 can have a proximal end that corresponds to a distal end of a locking component (such as locking components 126, 326, 426 of FIGS. 1-4C) to facilitate maintaining the position of the locking component or the insert 622. In some examples, the features described with regard to FIG. 6 can be applied to any of the variable angle locking systems described with reference to FIGS. 1-5B.

In the foregoing Detailed Description, it can be seen that various features are grouped together in a single example for the purpose of streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus the following claims are hereby incorporated into the Detailed Description, with each claim standing on its own as a separate example.

Note that not all of the activities or elements described above in the general description are required, that a portion of a specific activity or device may not be required, and that one or more further activities may be performed, or elements included, in addition to those described. Still further, the order in which activities are listed are not necessarily the order in which they are performed. Also, the concepts have been described with reference to specific examples. However, one of ordinary skill in the art appreciates that various modifications and changes can be made without departing from the scope of the present disclosure as set forth in the claims below. Accordingly, the specification and figures are to be regarded in an illustrative rather than a restrictive sense, and all such modifications are intended to be included within the scope of the present disclosure.

Benefits, other advantages, and solutions to problems have been described above with regard to specific examples. However, the benefits, advantages, solutions to problems, and any feature(s) that may cause any benefit, advantage, or solution to occur or become more pronounced are not to be construed as a critical, required, or essential feature of any or all the claims. Moreover, the particular examples disclosed above are illustrative only, as the disclosed subject matter may be modified and practiced in different but equivalent manners apparent to those skilled in the art having the benefit of the teachings herein. No limitations are intended to the details of construction or design herein shown, other than as described in the claims below. It is therefore evident that the particular examples disclosed above may be altered or modified and all such variations are considered within the scope of the disclosed subject matter. Accordingly, the protection sought herein is as set forth in the claims below.

What is claimed is:

1. A system comprising:
    an intramedullary nail; and
    an insert dimensioned to be positioned within the intramedullary nail, the insert including a rotating component configured to rotate about a rotational axis transverse to a longitudinal axis of the intramedullary nail;
    wherein the rotating component is configured to receive a bone screw, rotate about the rotational axis until the bone screw is positioned at a selected angle of a plurality of angles relative to the intramedullary nail, and deform to lock the bone screw at the selected angle.

2. The system of claim 1, wherein the intramedullary nail comprises an elongated hole configured to receive the bone screw at any of the plurality of angles.

3. The system of claim 1, wherein the insert is configured to be inserted into the intramedullary nail.

4. The system of claim 1, wherein the insert further comprises:
    a locking component configured to deliver a force to the rotating component such that the rotating component deforms around the bone screw to lock the bone screw at the selected angle.

5. The system of claim 1, wherein the plurality of angles has a range of at least 20 degrees.

6. The system of claim 1, wherein the rotating component comprises:
    at least one slot that reduces in size as the rotating component is compressible into the at least one slot.

7. The system of claim 6, wherein at least a portion of the at least one slot extends transverse to the longitudinal axis of the intramedullary nail.

8. A system comprising:
    an intramedullary nail; and
    an insert configured to be positioned within the intramedullary nail, the insert comprising:
        a rotating component configured to pivot about a rotational axis transverse to a longitudinal axis of the intramedullary nail, the rotating component defining an insert through bore and at least one slot; and a locking mechanism positioned at a proximal end of the rotating component;
wherein the insert through bore is configured to receive a bone screw, the rotating component is configured to rotate about the rotational axis such that the bone screw is positioned at a selected angle, and the locking mechanism is configured to compress the rotating component into the at least one slot to lock the bone screw at the selected angle.

9. The system of claim 8, wherein the rotating component comprises a non-metal material.

10. The system of claim 8, wherein the rotating component comprises a resorbable material.

11. The system of claim 8, wherein the rotating component comprises titanium.

12. The system of claim 8, wherein the insert through bore is configured to align with a nail through bore to define a channel to allow passage of the bone screw therethrough.

13. The system of claim 8, wherein the insert through bore comprises one or more internal threads configured to engage one or more external threads of the bone screw.

14. The system of claim 8, wherein the insert defines a variable angle screw trajectory with two rotational degrees of freedom.

15. The system of claim 8, wherein the rotating component is configured to rotate about the longitudinal axis of the intramedullary nail.

16. A system comprising:
an intramedullary nail including a nail longitudinal axis and comprising an inner diameter defining a nail lumen; and
an insert dimensioned to be positioned within the nail lumen, the insert comprising:
a rotating component configured to rotate about a rotational axis transverse to the nail longitudinal axis to provide a variable angle trajectory for a bone screw, the rotating component defining a slot; and
a locking mechanism configured to compress the rotating component to reduce a size of the slot and lock the bone screw at a patient-specific angle.

17. The system of claim 16, wherein the intramedullary nail is a humeral nail and the bone screw is a calcar screw, and the insert is configured to lock the calcar screw at the patient-specific angle corresponding to a patient-specific calcar area of a patient's humeral head.

18. The system of claim 16, wherein the insert is configured to be positioned entirely within the nail lumen of the intramedullary nail.

19. The system of claim 16, wherein the insert comprises a lumen along the nail longitudinal axis.

20. The system of claim 16, wherein the rotating component is configured to rotate about the nail longitudinal axis to provide the variable angle trajectory for the bone screw.

* * * * *